US012605154B2

(12) United States Patent
Willard et al.

(10) Patent No.: US 12,605,154 B2
(45) Date of Patent: Apr. 21, 2026

(54) MULTIPLE IMPLEMENT OPERATION AND COORDINATION USING SINGLE ACTUATOR FOR MEDICAL DEVICES

(71) Applicant: ConMed Corporation, Largo, FL (US)

(72) Inventors: Benjamin Willard, Clearwater, FL (US); Jeffrey T. Smith, Tampa, FL (US)

(73) Assignee: ConMed Corporation, Largo, FL (US)

( * ) Notice: Subject to any disclaimer, the term of this patent is extended or adjusted under 35 U.S.C. 154(b) by 29 days.

(21) Appl. No.: 18/294,004

(22) PCT Filed: Oct. 26, 2022

(86) PCT No.: PCT/US2022/047863
§ 371 (c)(1),
(2) Date: Jan. 31, 2024

(87) PCT Pub. No.: WO2023/076367
PCT Pub. Date: May 4, 2023

(65) Prior Publication Data
US 2024/0335192 A1     Oct. 10, 2024

Related U.S. Application Data

(60) Provisional application No. 63/321,062, filed on Mar. 17, 2022, provisional application No. 63/220,735, filed on Oct. 26, 2021.

(51) Int. Cl.
*A61B 17/04*     (2006.01)
*A61B 17/00*     (2006.01)
(Continued)

(52) U.S. Cl.
CPC .... *A61B 17/0469* (2013.01); *A61B 17/06066* (2013.01); *A61B 34/71* (2016.02);
(Continued)

(58) Field of Classification Search
CPC ............ A61B 17/0469; A61B 17/0482; A61B 17/06109; A61B 17/0483; A61B 17/0485;
(Continued)

(56) References Cited

U.S. PATENT DOCUMENTS 5,779,648 A     7/1998   Banik
5,817,111 A  *  10/1998  Riza ................. A61B 17/06109
                                                    606/139
(Continued)

FOREIGN PATENT DOCUMENTS

EP          2537472 A1    12/2012
JP        2013006000 A     1/2013

OTHER PUBLICATIONS

International Search Report and Written Opinion of PCT/US2022/047863, filed Oct. 26, 2022. pp. 1-11. Mailing date of Search Report, Feb. 21, 2023.
(Continued)

*Primary Examiner* — Tuan V Nguyen
(74) *Attorney, Agent, or Firm* — Bond, Schoeneck & King, PLLC; David L. Nocilly

(57)                    ABSTRACT

A system for a medical device that can operate multiple actuated implements with sophisticated and individual motion profiles using a single user actuator. The system has a handle having a pair of slots for each implement and an actuator positioned in the handle for movement between a first position and a second position that has a groove for each implement. Each implement is coupled to the handle a barrel that is captured in the pair of slots and driven by the groove of the actuator. The shape of the pair of slots and the corresponding groove combine to provide a motion profile for the implement that is independent from any other implement having its own pair of slots and groove. Multiple implements may thus be driven simultaneously and can have
(Continued)

complex and coordinated movement based on user operation
of the single actuator.

20 Claims, 14 Drawing Sheets

(51) Int. Cl.
A61B 17/06 (2006.01)
A61B 34/00 (2016.01)
(52) U.S. Cl.
CPC ............... *A61B 2017/00358* (2013.01); *A61B 2034/715* (2016.02)
(58) Field of Classification Search
CPC .... A61B 2017/00309; A61B 2017/047; A61B 2017/06052
See application file for complete search history.

(56) References Cited

U.S. PATENT DOCUMENTS

| | | |
|---|---|---|
| 2009/0312603 A1 | 12/2009 | Lummis et al. |
| 2011/0295279 A1* | 12/2011 | Stone ................ A61B 17/0482 |
| | | 606/145 |
| 2014/0207158 A1 | 7/2014 | Stone et al. |

OTHER PUBLICATIONS

JP First Office Action, Application No. 2024-518626, dated Feb. 18, 2025, entire document.

* cited by examiner

MULTIPLE IMPLEMENT OPERATION AND COORDINATION USING SINGLE ACTUATOR FOR MEDICAL DEVICES

CROSS-REFERENCE TO RELATED APPLICATIONS

The present application claims priority to U.S. Provisional Application No. 63/220,735, filed on Oct. 26, 2021, and U.S. Provisional Application No. 63/321,062 filed on Mar. 17, 2022.

TECHNICAL FIELD

The present disclosure relates to medical devices and, more particularly, to an approach for operating and coordinating movement of multiple implements in a medical device with a single user actuator.

DESCRIPTION OF THE RELATED ART

A medical device can have multiple actuated implements (such as formed wire implements, machined implements, tubular implements, etc.) that each require sophisticated and individual motion profiles with respect to each other and with respect to their actuators (such as a button, slider, lever, etc.), including movement in concert with each other, to allow a medical device to perform a particular task.

BRIEF SUMMARY

The inventors recognize that there are limitations associated with conventional or existing medical devices with multiple actuated implements (as discussed above). Conventional approaches require the use of multiple actuators and rely on the user to properly time and coordinate the action of the multiple implements. These approaches also lack any the ability to control the relative speed of operation of the multiple implements and the amount of force of operation being applied, including instances where one implement may need to temporarily stop until another implement has moved into place. Accordingly, there is a need for an improved approach for operating multiple implement medical devices that can control the operation of multiple implements, coordinate the relative movement of those implements, and control the speed of movement and forces involves, all through the use of a single user operated actuator. In the various aspects of the design, sophisticated motion profiles for one or more actuated implements can be accomplished with just one single movement of an actuator by the user, thereby allowing more complex motions of multiple actuated implements to be performed, yielding greater simplicity of use for the user of the medical device, reducing potential for error by the user, and allowing functionality of a medical device that would not be otherwise attainable due to the inability of a user to perform the requisite complex and coordinated movements manually.

In one aspect, a medical device has a handle having a first pair of slots and a second pair of slots, an actuator positioned in the handle for movement between a first position and a second, wherein the actuator includes a first groove and a second groove, a first implement connected to a first barrel that extends between and is positioned in the first pair of slots of the handle and is captured in the first groove of the actuator, and a second implement connected to a second barrel that extends between and is positioned in the second pair of slots of the handle and captured in the second groove of the actuator. The first groove may have a first shape and the second groove may have a second shape that is different than the first shape. The first pair of slots may define a first path and the second pair of slots may define a second path that is different than the first path. Movement of the actuator between the first position and the second position cause the first groove to drive the first barrel to translate along the first path of the first pair of slots and the second groove to drive the second barrel to translate along the second path of the second pair of slots. Movement of the actuator between the first position and the second position causes the first implement to move in a first motion profile and the second implement to move in a second motion profile that is different than the first motion profile.

In another aspect, a piercing needle that can entrap a suture is formed by a handle having a first pair of slots and a second pair of slots, an actuator positioned in the handle for movement between a first position and a second, wherein the actuator includes a first groove and a second groove, a hook connected to a first barrel that extends between and is positioned in the first pair of slots of the handle and is captured in the first groove of the actuator, and a lasso connected to a second barrel that extends between and is positioned in the second pair of slots of the handle and captured in the second groove of the actuator. The first groove may have a first shape and the second groove may have a second shape that is different than the first shape. The first pair of slots may define a first path and the second pair of slots may define a second path that is different than the first path. Movement of the actuator between the first position and the second position cause the first groove to drive the first barrel to translate along the first path of the first pair of slots and the second groove to drive the second barrel to translate along the second path of the second pair of slots. Movement of the actuator between the first position and the second position causes the hook to move in a first motion profile and the lasso to move in a second motion profile that is different than the first motion profile.

In a further aspect, a method of independently controlling at least two implements via a single user action is performed by providing a medical device including a handle having a first pair of slots and a second pair of slots, an actuator positioned in the handle for movement between a first position and a second, wherein the actuator includes a first groove and a second groove, a first implement connected to a first barrel that extends between and is positioned in the first pair of slots of the handle and is captured in the first groove of the actuator, and a second implement connected to a second barrel that extends between and is positioned in the second pair of slots of the handle and captured in the second groove of the actuator. A button coupled to the actuator may then be used to move the actuator between the first position and the second position so that the first groove drives the first barrel to move within the first pair of slots and the second groove to move within the second pair of slots, wherein movement of the first barrel drives movement of the first implement and movement of the second barrel drives movement of the second implement. Movement of the first barrel is controlled by a first shape of the first groove and movement of the second barrel is controlled by a second shape of the second groove that is different than the first shape. Movement of the first barrel is additionally controlled by a first path of the first pair of slots and movement of the second barrel is additionally control by a second path of the second pair of slots that is different than the first path. Movement of the actuator between the first position and the second position causes the first groove to drive the first barrel to translate along the first path of the first pair of slots and the second groove to drive the second barrel to translate along the second path of the second pair of slots. Movement of the actuator between the first position and the second position causes the first implement to move in a first motion profile and the second implement to move in a second motion profile that is different than the first motion profile. The medical device of the method may be a piercing needle where the first implement is a hook and the second implement is a lasso. Movement of the actuator between the first position and the second position causes the hook and the lasso to capture a suture positioned proximately to a tip of the piercing needle. The hook and the lasso capture the suture by the hook moving through a first motion profile and the lasso moving through a second motion profile that is different than the first motion profile when the actuator is moved from the first position to the second position.

BRIEF DESCRIPTION OF THE SEVERAL VIEWS OF THE DRAWING(S)

FIG. 3A is a perspective view of an exemplary medical device showing two actuated implements that are moved in a coordinated manner into a second position where an object such as a suture is captured.

DETAILED DESCRIPTION

Figure 1:
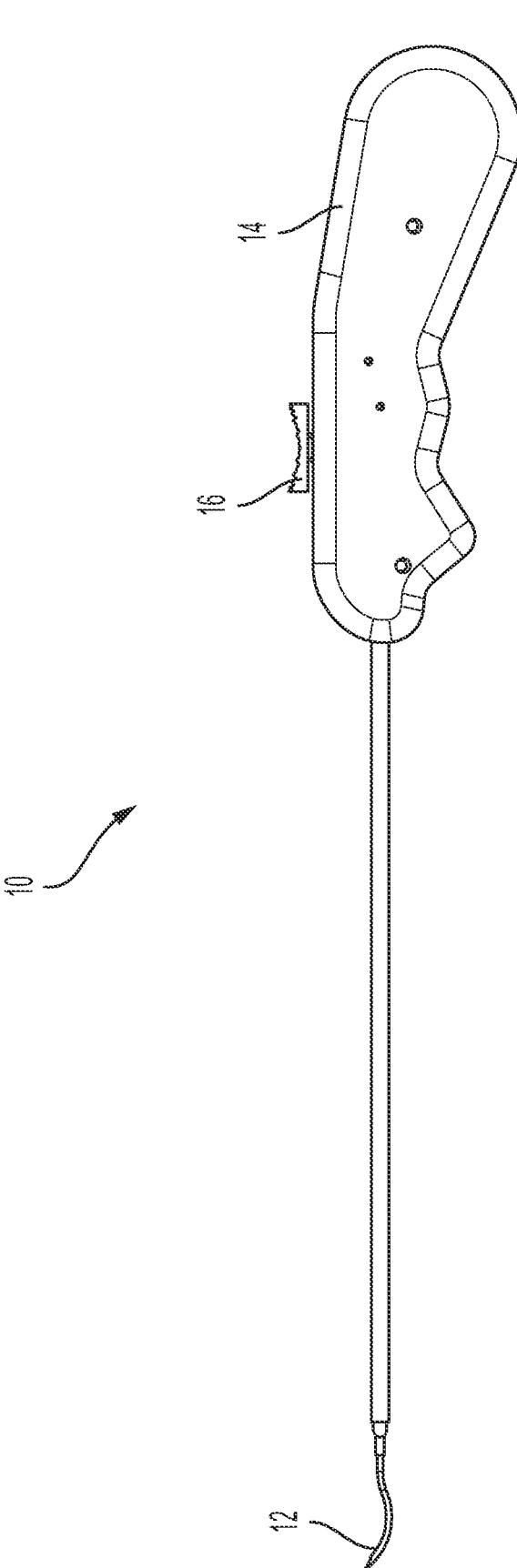
FIG. 1 is a side view of an exemplary medical device outfitted for the controlled and coordinated movement of multiple implements via a single actuator.

Referring to the figures, wherein like numerals refer to like parts throughout, there is seen in FIG. 1 an example of a system 10 for providing movement of multiple actuated implements 12 in a medical device 14 via user operation of a single, user operated actuator 16. System 10 can provide complex motion profiles with multiple speeds, multiple forces, and intricate coordinated movement. In the figures, system 10 is illustrated for use with a labral suture passer, such as that used in arthroscopic hip labral repair surgeries, but can used in conjunction with many different types of medical devices having multiple actuated implement that require different motion profiles, including coordination between the actuated implements, all through the use of a single user actuator.

Figure 2:
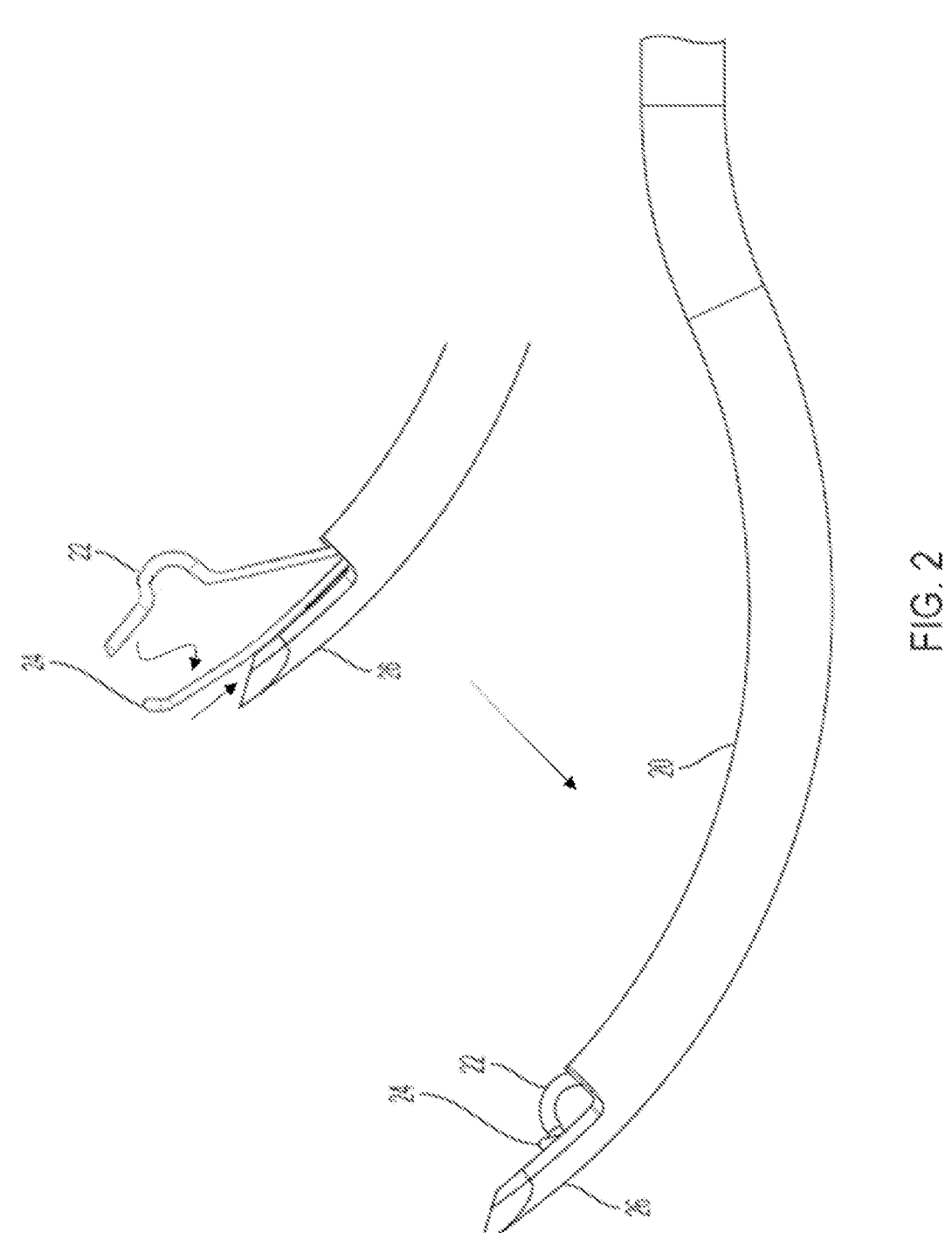
FIG. 2 is a partial side view of an exemplary medical device showing two actuated implements that are moved in a coordinated manner.
Figures 3A, 3B, 3C:
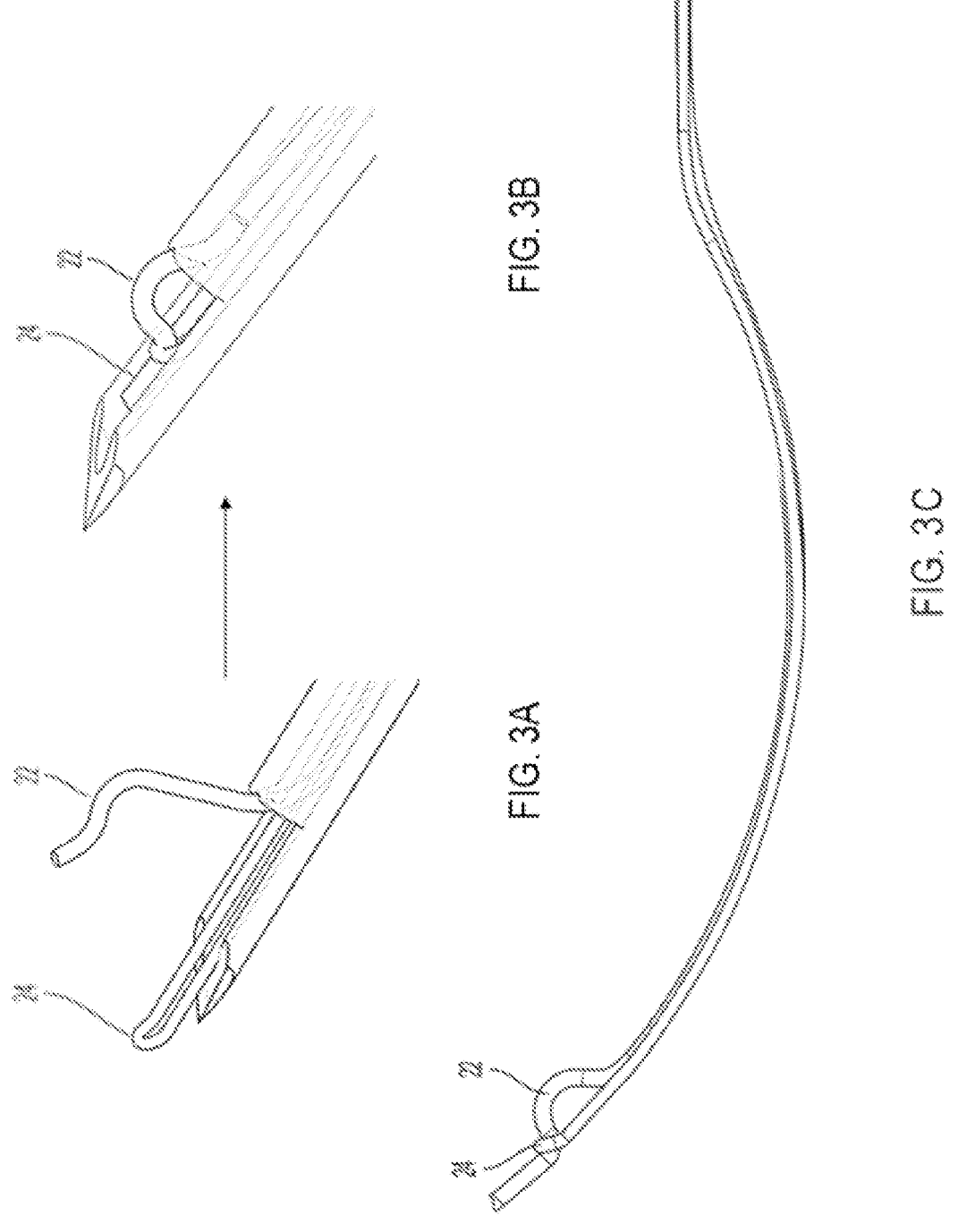
FIG. 3A is a perspective view of an exemplary medical device showing two actuated implements that are moved in a coordinated manner into a first position for capturing an object such as a suture.
FIG. 3C is a partial side view of two actuated implements of an exemplary medical device that are moved in a coordinated manner show in a captured and interlocked relationship.

Medical device 14 includes a curved piercing cannulated needle 20, seen in FIG. 2, which houses two implements 12, i.e., a hook 22 and a lasso 24 that extend from a tip 26 of needle 20 to cooperate and entrap a suture. In the example of a suture passer as medical device 14, hook 22 can be extended separately from lasso 24, such as by including a prebend in wire of lasso 24 and/or the hook to form a suture capturing opening between hook 22 and lasso 24. As further seen in FIG. 2, hook 22 and lasso 24 can be retracted independently and through different motion profiles so that any suture positioned between hook 22 and lasso 24 remains trapped therein as hook 22 is captured in the end of lasso 24 and both are withdrawn into piercing needle 20, thereby securely grasping suture. As seen in FIG. 3A through 3C, hook 22 and lasso 24 are formed from resilient wire and are formed so that they will spring into a predetermined configuration when extended from tip 26 that assists in the capture of a suture, and will interlock with hook 22 captured in lasso 24 when withdrawn into needle 20. In order to capture the suture, hook 22 and lasso 24 are moved independently of each other and through different motion profiles, i.e., with different distances traverses, different speeds of motion, and different forces applied, to most effectively capture the suture and return at least partially back into tip 26 to securely grasp the suture. When suture is entrapped, it is captured by hook 22, such as in a bend or other feature as seen in FIG. 3C, and prevented from escape by loop 24. It should be recognized that the bend or contour in hook 22 may be of sufficient size and cross-section to admit suture while still allowing suture to slide in a transverse direction, as to permit the user to manually slide suture after capture. Alternatively and additionally, when the bend or aperture of hook 22 is retracted into the cannulation of shaft 20 in a proximal direction to a magnitude that shaft 20 occludes or partially occludes the aperture or bend, this retraction will pinch the suture and apply sufficient force to it that makes sliding of the suture in a transverse direction no longer possible, thereby providing a suture holding function. Medical device 14 could include different implements, such as cutting blades, jaws, or pivotal joints, and thus implements can be constructed from structures other than the wires seen in FIG. 3 as an example of system 10.

Figure 4:
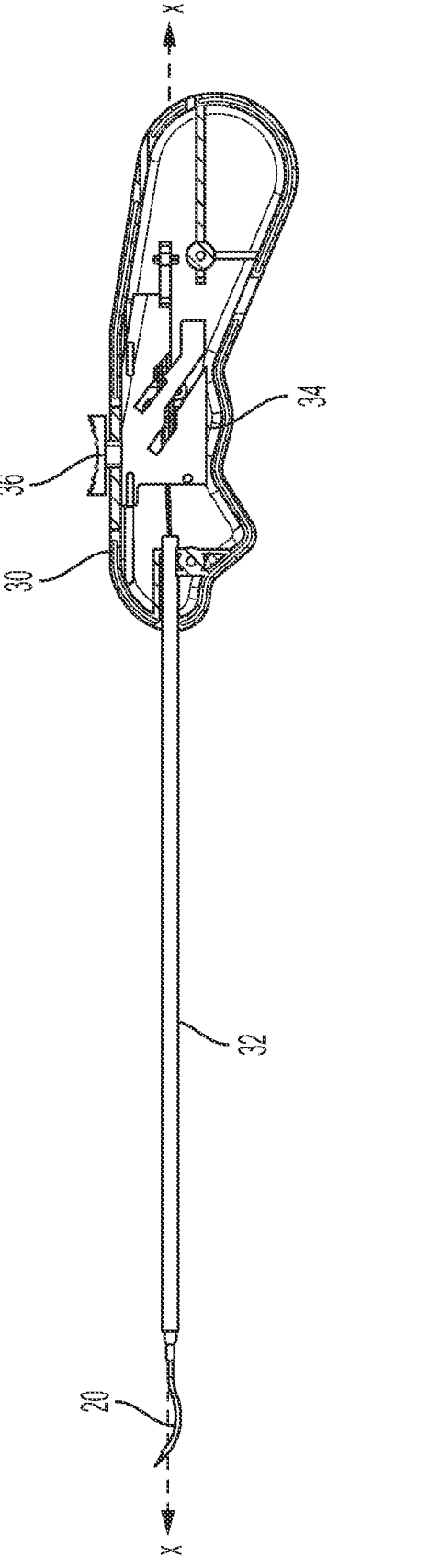
FIG. 4 is a side view of a partially disassembled exemplary medical device outfitted for the controlled and coordinated movement of multiple implements via a single actuator.

Referring to FIG. 4, handle 30 of medical device 14 is coupled via a shaft 32 to needle 20 to allow a user to manually direct and position needle 20. Handle 30 includes an actuator 34 having a user accessible button 36 extending outwardly from handle 30 that can be moved by user and, in the example of FIG. 4, the movement illustrated as in parallel to the longitudinal axis X-X of medical device 14 but can be in any direction relative to medical device 14 such as diagonally or transversely. Handle 30 is shown as a two-piece construction with one side removed for illustration purposes, but it should be recognized that the opposing side of handle 30 will be a mirror image of the side shown in FIG. 4. Handle 30 could also be asymmetric provided that the assembly of any asymmetric pieces result in the structure described herein.

Figure 5:
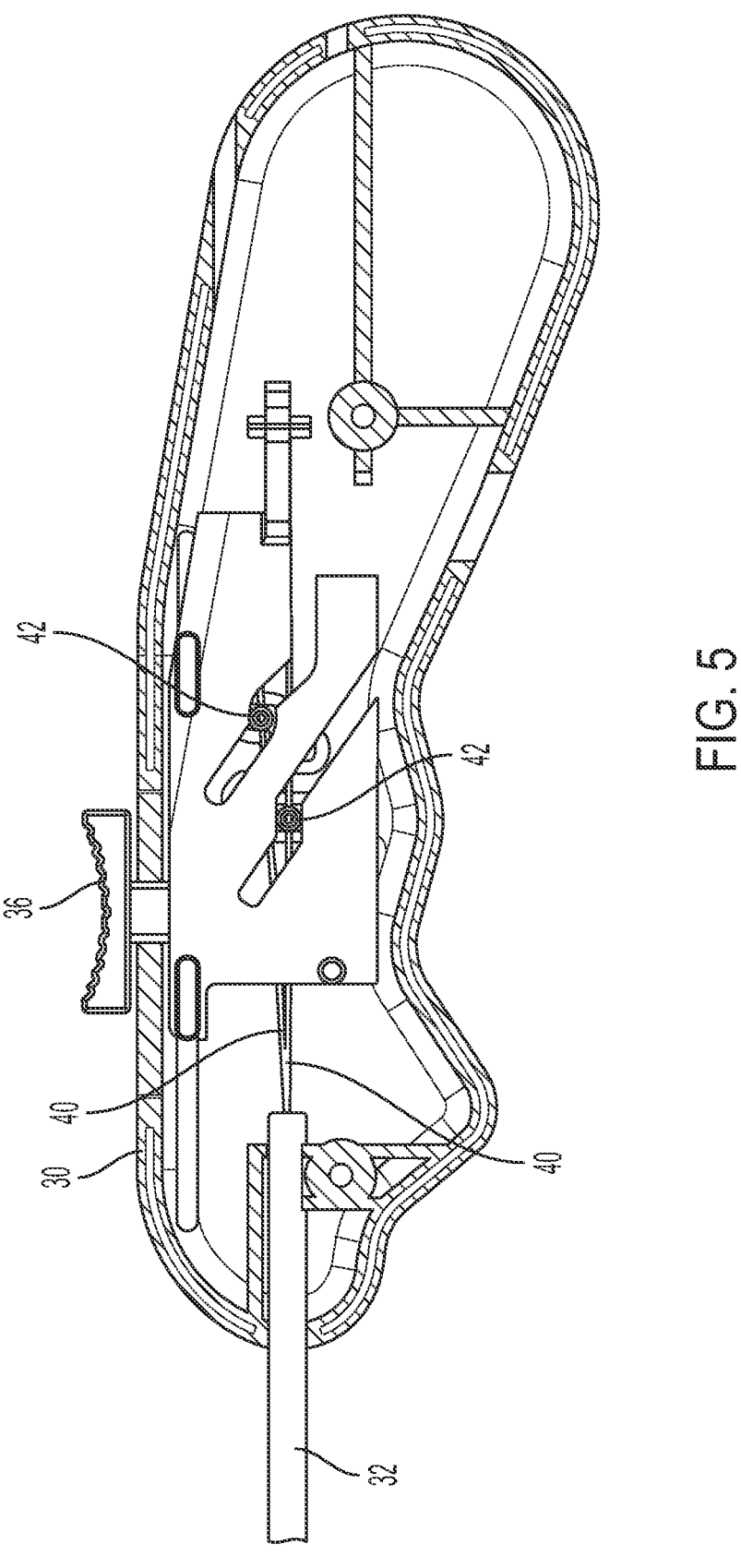
FIG. 5 is a side view of a partially disassembled medical device handle outfitted for the controlled and coordinated movement of multiple implements via a single actuator.

Referring to FIG. 5, each implement to be independent operated and controlled by system 10 is interconnected to handle 30 by a wire 40 that extends through shaft 32 and is secured to a barrel 42 that extends transversely across the interior of handle 30. Although the present example has two implements and thus two wires 40 and two barrels 42, medical device 14 may include additional implements with corresponding wires 40 and barrels 42. Hook 22 and lasso 24 are each coupled at their proximal ends to handle 30 via a corresponding barrel 42 that extend transversely across handle 30. As hook 22 and lasso 24 are formed from wires, they are shown as connected directly to barrels 42, but non-wire implements can be connected to handle 30 using dedicated wires 40. It should be recognized that different structures could be used in lieu of wires as long as such structures are rigid enough to transmit the forces in the same manner as wires.

Figure 6:
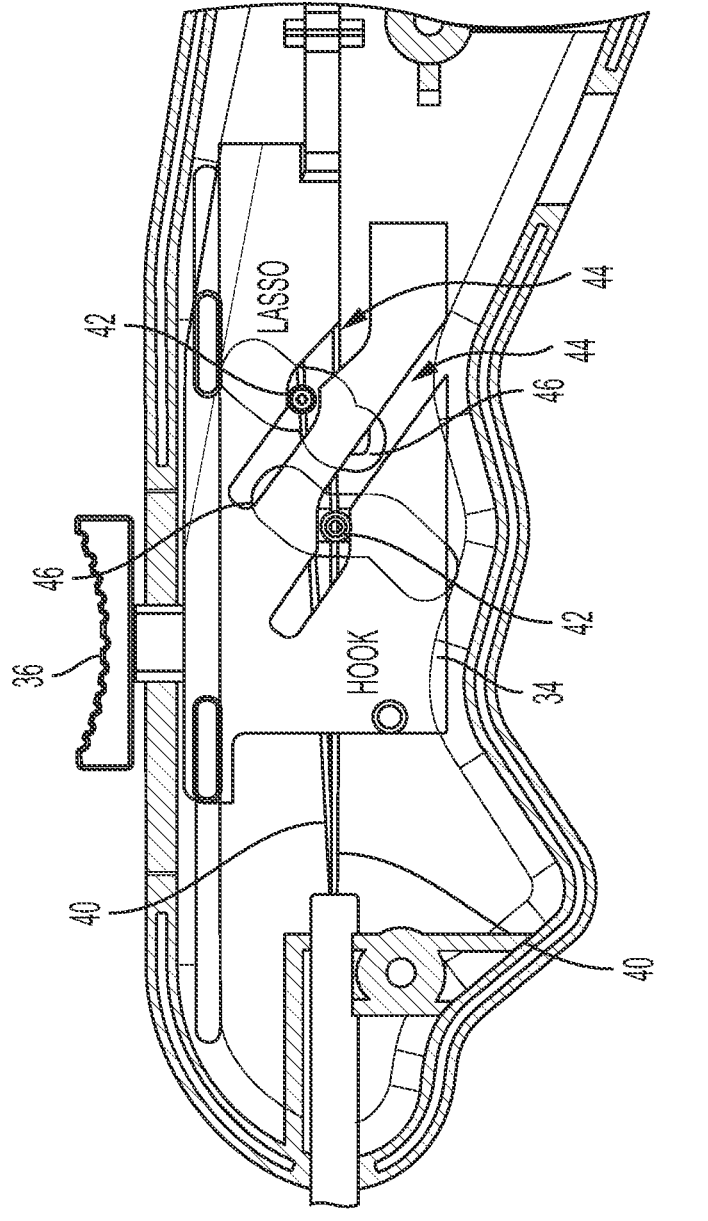
FIG. 6 is another side view of a partially disassembled medical device handle outfitted for the controlled and coordinated movement of multiple implements via a single actuator.
Figure 7:
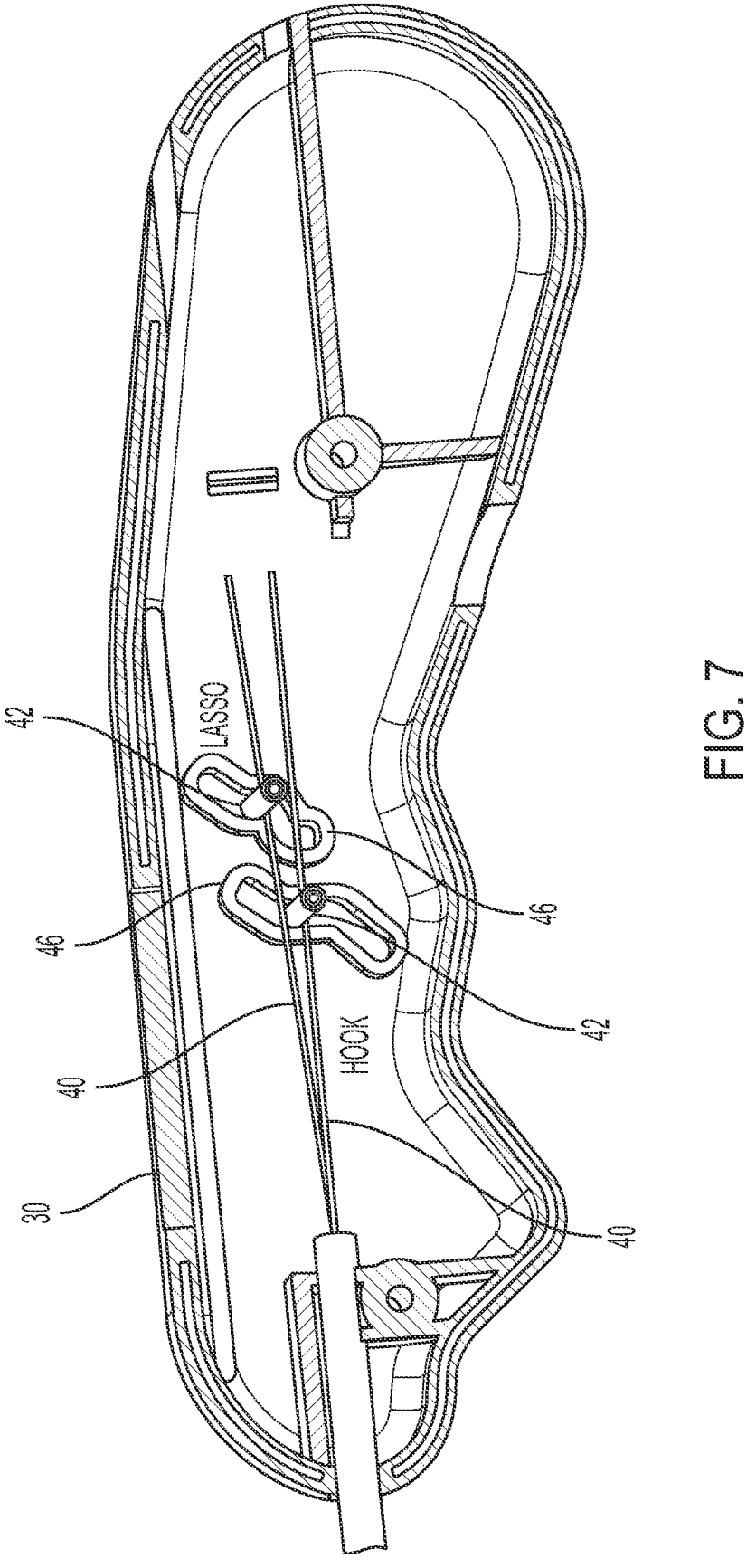
FIG. 7 is a perspective view of an actuator for the controlled and coordinated movement of multiple implements via a single actuator.

Referring to FIGS. 6 and 7, the intermediate portion of each barrel 42 is captured in a corresponding groove 44 formed in actuator 34 and the ends of each barrel 42 are captured in opposing slots 46 formed into the interior surface of each side of handle 30. The shape of each groove 44 and the path defined by corresponding slots 46 control movement of the barrel 42 captured in that groove 44 and those slots 46 when actuator 34 is moved by a user. Grooves 44 have a specific contour that bears against barrels 42 and thus can thus apply a force to barrels when actuator 34 is moved so that barrels 42 translate along their respective slots 46. The angle of the paths formed by grooves 44 will thus cause grooves 44 to apply a force to barrels 42 when actuator 34 is moved by a user, although the force being applied to barrels 42 can be zero if grooves 44 extend along the same axis and the axis of movement of actuator 34, illustrated as parallel to axis X-X for simplicity. As further seen in FIG. 6. grooves 44 may be independently shaped from each other to provide different forces at different points of the movement of actuator 34. As further seen in FIG. 7, slots 46 on the insider of handle 30 also extend along a predetermined path that governs the movement of barrels 42 in response to the forces provided by grooves 44, and each slot 46 may have a different path geometry so that the movement of barrels 42 in slots 46 are independently controlled.

Figure 8:
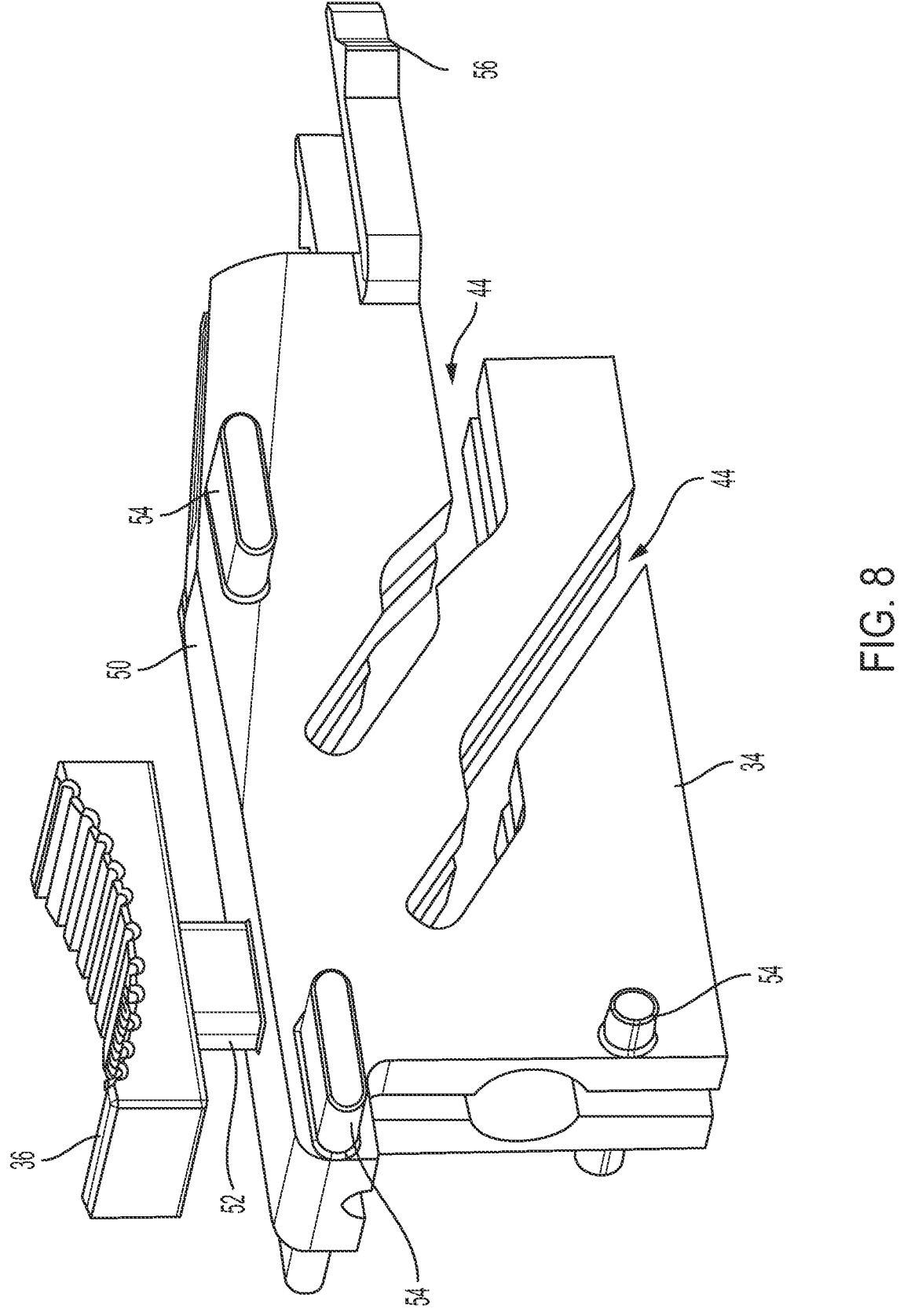
FIG. 8 is a side view of a handle coupled to multiple actuated implements.

Referring to FIG. 8, actuator 34 may comprise a body 50 defining grooves 44 and having a post 52 that can extend from handle 30 to support user button 36. Body 50 may include any number of outwardly extending features 54 that slidingly engage the inside of handle 30 to provide stability to actuator 34 and to allow actuator 34 to slide along the inside handle 30 in response to a force applied to button 36 by a user. Actuator 34 may also include a latch 56 for releasable capturing actuator 34 in a home position within handle 30.

Figure 9:
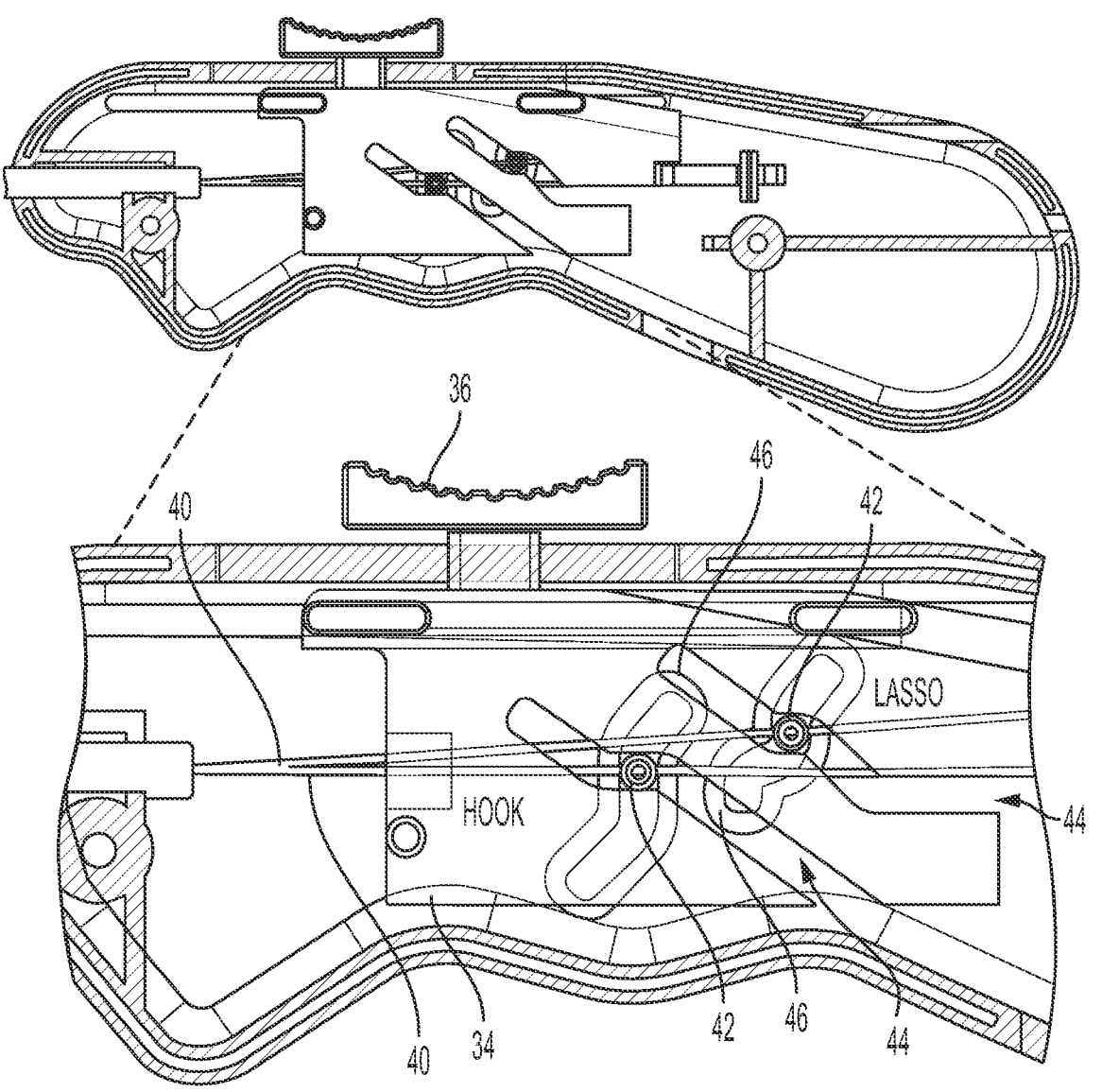
FIG. 9 is a side view of with the actuator partially transparent to show the interaction of the grooves and slots.

Referring to FIG. 9, barrels 42 will be positioned at a particular location inside the handle 30 where the groove 44 of the actuator 34 for a given barrel 42 crosses the corresponding slot 46 of handle 30 for that barrel 42. Each barrel 42 thus resides at a location determined by the intersection of the given groove 44 of actuator 34 and the corresponding slot 46 of handle 30. The particular and relative geometries of grooves 44 and slots 46 may thus provide a number of advantageous operations, as explained herein.

Figure 10:
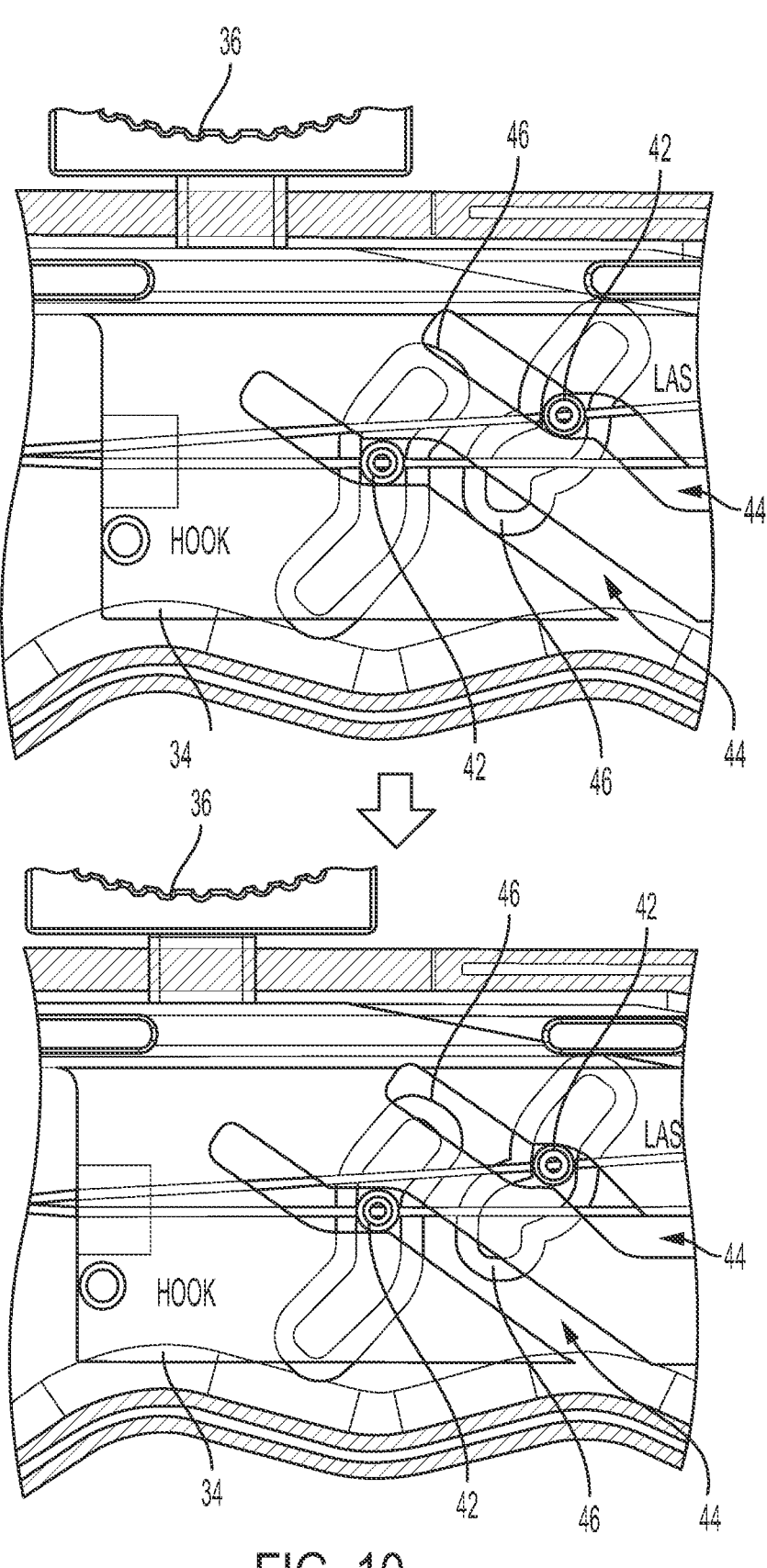
FIG. 10 are first and second side views of the relevant portions of the inside of the handle showing the positioning of the relevant structure in response to a user actuator moving from a first position in the first view to a second position in the second view.

Referring to FIG. 10, system 10 can cause one or more of the actuated implements to stop moving despite continued movement of actuator 34. When it is desired for an implement to stop moving, the corresponding groove 44 can extend in parallel to the motion of actuator 34, illustrated as along longitudinal axis X-X of the device. For example, as seen in FIG. 10, the movement of actuator 34 horizontally to the left from the top panel to the bottom panel does not result in any movement of either barrel 42 as grooves 44 extend in the same direction as the movement of actuator 34 (shown in FIG. 10 as horizontal) and slots 46 extend at right angles to the direction of movement (shown in FIG. 10 as vertical). System 10 may thus provide a dead band in the movement of actuator 34 where no corresponding motion occurs to the implements.

Figure 11:
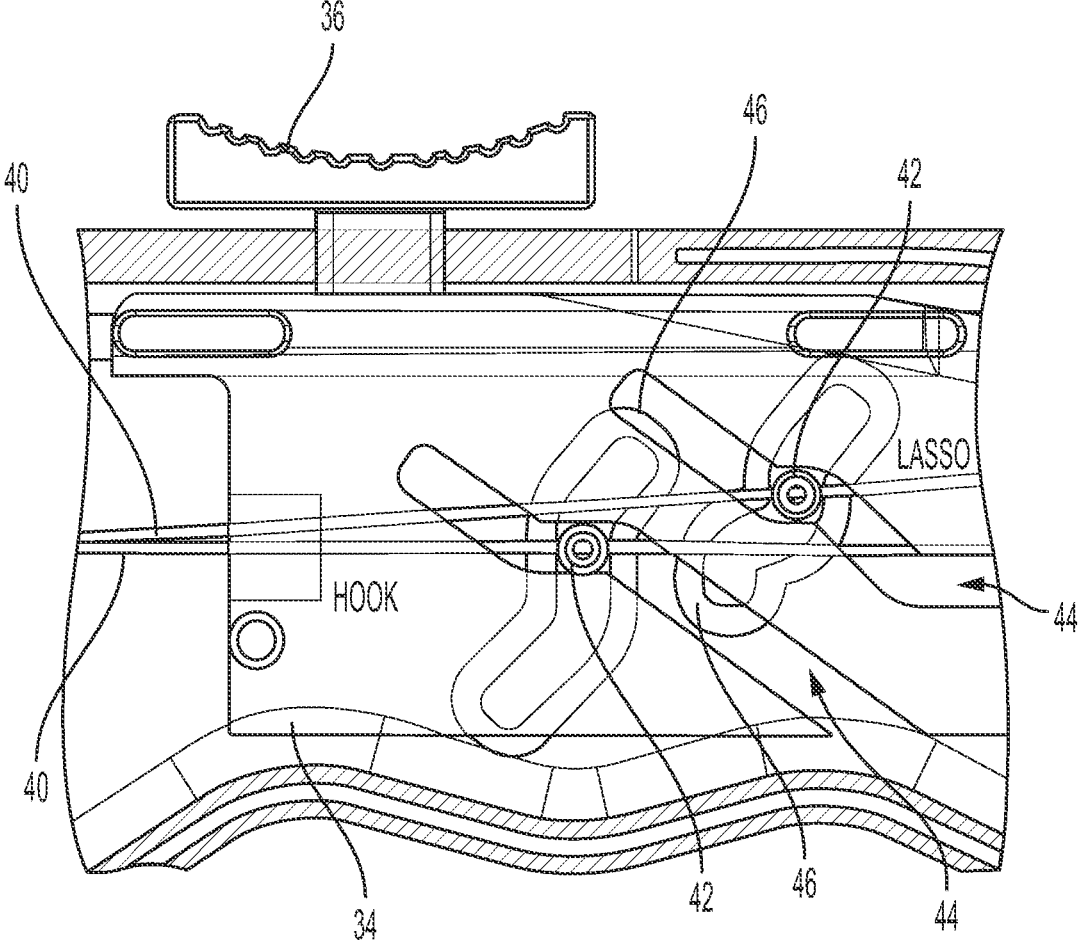
FIG. 11 is a side view of the relevant portions of the inside of the handle showing an arrangement that prevents back driving of the actuated implements.

Referring to FIG. 11, system 10 can be configured to provide positions where the actuated implement cannot be back by the application of any load to the actuated implement. As seen in FIG. 11, the positioning of barrels 42 in a location where grooves 44 are parallel to the direction of motion and slots 46 are perpendicular to the direction of motion (shown as horizontal and vertical, respectively) any axial force applied to wires 40 will cause barrels 42 to press into the vertical (perpendicular) wall of slot 46 and, as a result, no motion of barrels can occur. Thus, when barrels 42 are in a position in the motion profile illustrated in FIG. 11, any implements connected to barrels 42 cannot be back driven.

Figure 12:
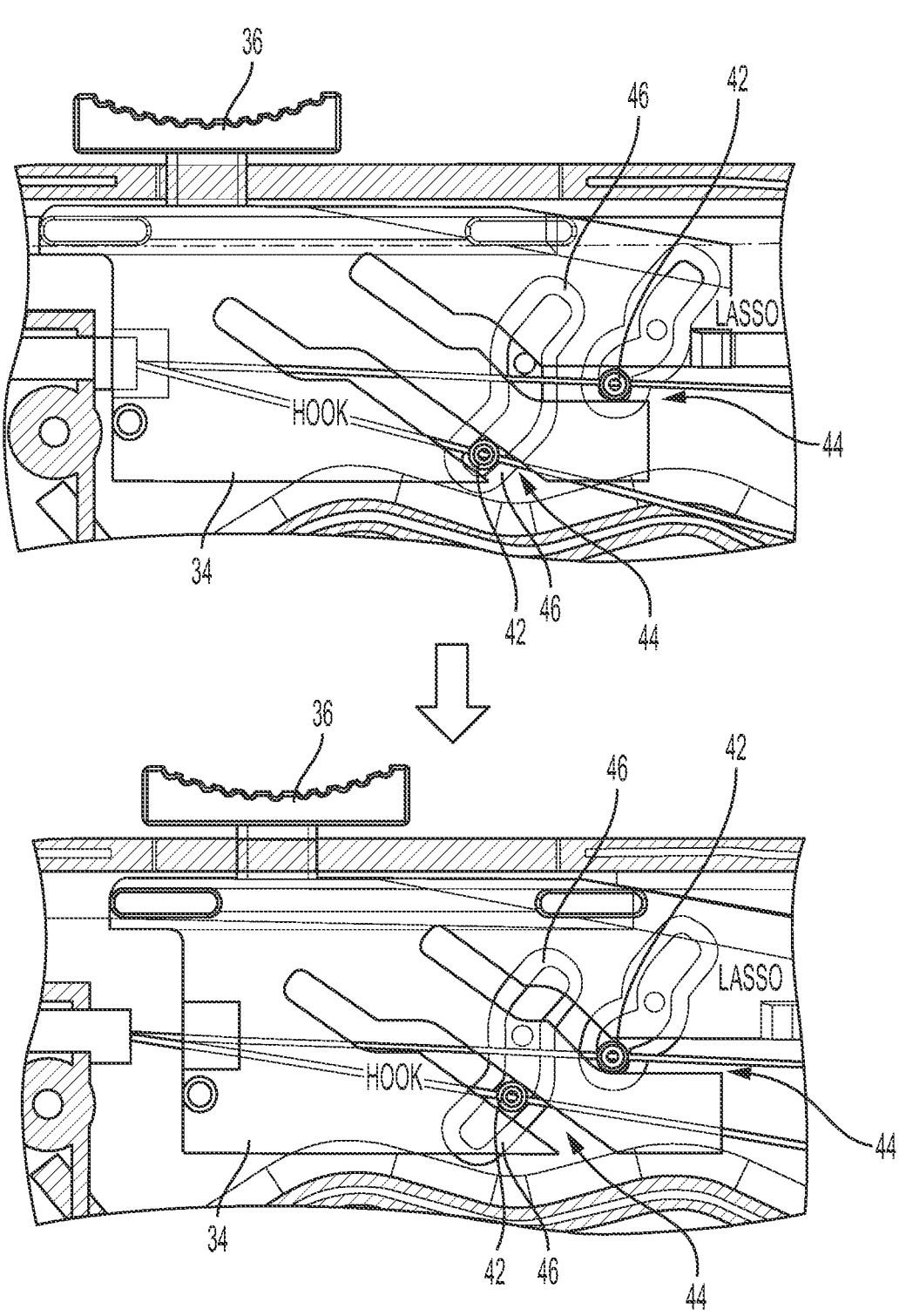
FIG. 12 are first and second side views of the relevant portions of the inside of the handle showing mechanical force amplification and speed reduction in response to a user actuator moving from a first position in the first view to a second position in the second view.

Referring to FIG. 12, system 10 can provide mechanical force amplification and mechanical speed reduction of the motion of the actuated implements relative to the input motion of actuator 34. When barrels 42 are in regions of grooves 44 and slots 46 that are inclined, but with a different amount of incline, barrels 42 will move differently. For example, when slot 46 of handle 30 is more steeply inclined than the corresponding groove 44, axial movement of actuator 34 yields a relatively small amount of vertical motion of barrel 42 in slot 46 and thus a smaller amount of axial travel of wires 40 coupled to barrel 42, thereby providing a mechanical advantage. More specifically, the forces produced by this arrangement is greater than forces input by the user of the device and the speed of motion of the actuated implement is less than the speed of motion of actuator 34 and thus provides a greater capacity for the user to create fine motions of an actuated implement.

Figure 13:
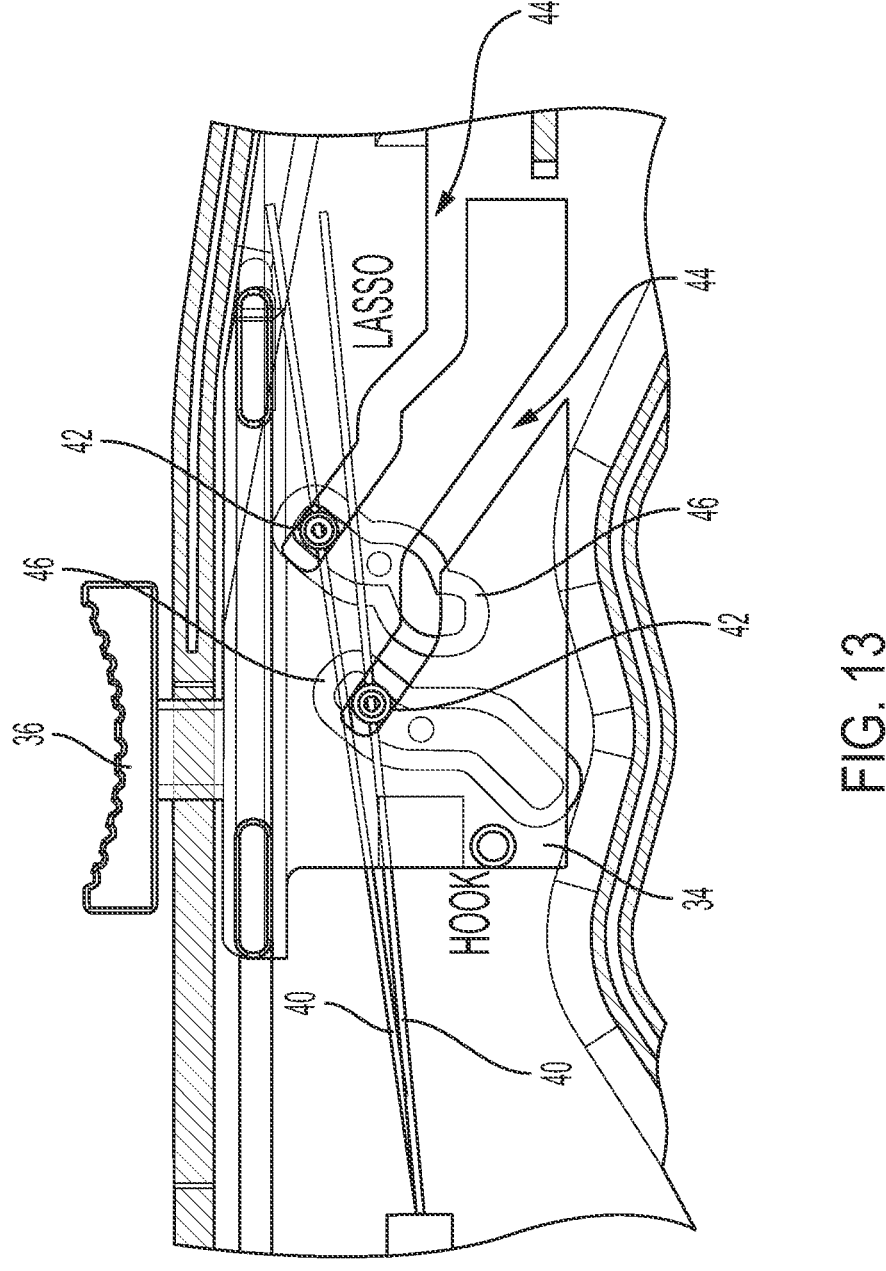
FIG. 13 is a side view of the relevant portions of the inside of the handle showing an arrangement that maintains the force applied to the actuated implements after a user has ceased applying a force to the user actuator.

Referring to FIG. 13, system 10 also allows for actuated implements to be moved into a location and then locked in place against further movement until actuator 34 is moved by the user. System 10 can thus provide a motion profile where actuated implements can be placed into a configuration where substantial forces are developed via motion, but the resting place of the implements once force application has ceased by the user is maintained by system 10 without any maintained user force input. Similar to the prevention of back driving, system 10 can employ grooves 44 that are shallow and slots that are steep so that when motion of a barrel 42 does occur (i.e., barrel 42 is not in a dwell region or a deadband), barrel 42 will maintain a force on the implement even if the force applied by the user is removed. As seen in FIG. 13, steep slots 46 (more vertical than horizontal, as shown) of handle 30 coupled with shallow grooves 44 (more horizontal than vertical, as shown) create a configuration where barrel 42 is locked in place by the tension applied to wires 40 because the angles of slots 46 are of a magnitude such that the arctangent of the angle of slot 46 relative to the direction of pull of wire 40 is less that the coefficient of friction of barrel in slot 46, making it impossible for barrel 42 to be back-driven (pulled to the left, in the image below) by tension on wire 40 that would pull barrel distally. As a result, a user can release actuator button 36 while retaining the force on barrels.

Figure 14:
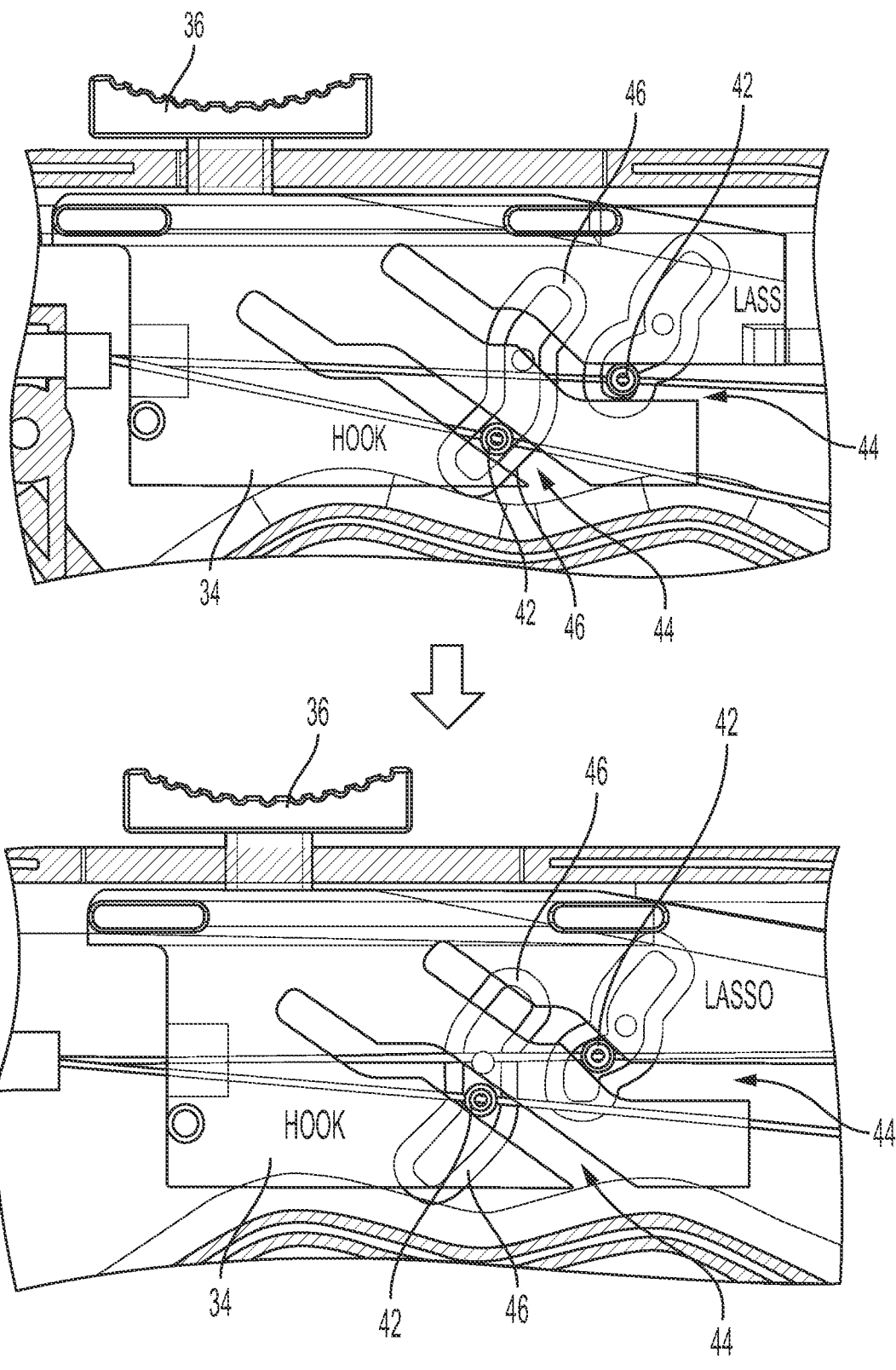
FIG. 14 are first and second side views of the relevant portions of the inside of the handle showing independent complex motion profiles for each actuated implement in response to a user actuator moving from a first position in the first view to a second position in the second view.

Referring to FIG. 14, system 10 can enable multiple actuated implements to perform multiple complex motion profiles in a coordinated fashion with only a single means of actuation applied by the user. As shown FIG. 14, movement of actuator to the distal position of the left panel from the more proximal position of the right panel, lower barrel 42 is in motion when the button is moved to the left, while the upper barrel 42 has only moved a minor distance into a region where no movement occurs. The motion of the upper barrel 42, although limited, was at a must faster rate than lower barrel 42 due to the different slopes of the corresponding grooves 44. Thus, system 10 can provide multiple slots 46 in handle 30 working in concert with multiple grooves 44 in button 36 so that each barrel 42 moves separately and independently, but can be coordinated with any other barrel 42 to achieve a desired effect.

While the description and figures describe and depict a crescent-shaped piercing element at the distal end of device 10, it is understood that arthroscopic, and more generally surgical procedures, frequently employ tip geometries specific to the needs of specific procedures, these may include but not be limited to large-radius sweeping arcs, straight piercing tips, straight piercing elements with relatively sharp bends along their length, piercing elements that in addition to bends in the sagittal plane of the device also incorporate bends left or right (transverse) to as well, and also various corkscrew-like shapes that pierce when applied to tissue in a rotary fashion.

While the description and figures describe and depict multiple wires 40 traveling axially back and forth down the inside diameter of shaft 34, it also foreseeable that the addition of a low-friction material, such as a sleeve inside the inside diameter of shaft 32 would serve to reduce friction of hook 22, loop 24 and wires 40 as they travel back and forth axially in device 10. Additionally it is foreseeable that having not just one cannulation in the bore of the low-friction sleeve but instead having two, three or even more cannulations where each cannulation in the low-friction sleeve would have only wire 40 in each cannulation, would afford improvements in the control of those wires 40 in the inside diameter of shaft 32, thereby yielding improvements in the accuracy, smoothness, and control of the elements of the invention manipulated by wires 40 with respect to the inputs made by the user via the user-operated-actuator 16.

Various medical devices with multiple actuated implements, all set into complex and coordinated motion profiles, can benefit from any number of the implements in the device being afforded a mechanical force multiplication relative to the force applied to the means of actuation at any part or portion of their motion profile, thereby allowing the actuated implements to develop forces that exceed the force input by the user via a means of actuation (such as a button, slider, lever, etc). Various medical devices with multiple actuated implements can also benefit from any actuated implement in the device being afforded a reduction in speed of movement relative to the actuator, such as in the case slowing down the speed of movement of one actuated implement to allow very fine movements of another actuated implement to take place in response to larger movements of the user actuator. The motion profile of each actuated implement can have varying speeds and forces, including periods where the actuated implement will stop or dwell completely despite movement user actuator to park an actuated implement in a specific position regardless of user actuation, thus creating a deadband where motion of the actuator yields zero movement of an actuated implement. The pathways discussed herein can include a variety of shapes and sizes tuned to a particular use of a medical device at issue (e.g., for more force, speed etc. as discussed herein). For instance, a pathway can be parallel to or angled from a central or other longitudinal axis of a body of the medical device (where applicable) or other portions of the medical device such as the device handle. A pathway can include parallel and/or different angled portions. Further, at least one pathway can have similar and/or different parallel and/or angled portions as compared to at least one other pathway in the device.

What is claimed is:

1. A medical device, comprising:
a handle having a first pair of slots and a second pair of slots;
an actuator positioned in the handle for movement between a first position and a second, wherein the actuator includes a first groove and a second groove;
a first implement connected to a first barrel that extends between and is positioned in the first pair of slots of the handle and is captured in the first groove of the actuator; and
a second implement connected to a second barrel that extends between and is positioned in the second pair of slots of the handle and captured in the second groove of the actuator.

2. The medical device of claim 1, wherein the first groove has a first shape and the second groove has a second shape that is different than the first shape.

3. The medical device of claim 2, wherein the first pair of slots define a first path and the second pair of slots define a second path that is different than the first path.

4. The medical device of claim 3, wherein movement of the actuator between the first position and the second position causes the first groove to drive the first barrel to translate along the first path of the first pair of slots and the second groove to drive the second barrel to translate along the second path of the second pair of slots.

5. The medical device of claim 4, wherein movement of the actuator between the first position and the second position causes the first implement to move in a first motion profile and the second implement to move in a second motion profile that is different than the first motion profile.

6. A piercing needle that can entrap a suture, comprising:
a handle having a first pair of slots and a second pair of slots;
an actuator positioned in the handle for movement between a first position and a second, wherein the actuator includes a first groove and a second groove;
a hook connected to a first barrel that extends between and is positioned in the first pair of slots of the handle and is captured in the first groove of the actuator; and

9 a lasso connected to a second barrel that extends between and is positioned in the second pair of slots of the handle and captured in the second groove of the actuator.

7. The piercing needle device of claim 6, wherein the first groove has a first shape and the second groove has a second shape that is different than the first shape.

8. The piercing needle device of claim 7, wherein the first pair of slots define a first path and the second pair of slots define a second path that is different than the first path.

9. The piercing needle device of claim 8, wherein movement of the actuator between the first position and the second position causes the first groove to drive the first barrel to translate along the first path of the first pair of slots and the second groove to drive the second barrel to translate along the second path of the second pair of slots.

10. The piercing needle device of claim 9, wherein movement of the actuator between the first position and the second position causes the hook to move in a first motion profile and the lasso to move in a second motion profile that is different than the first motion profile.

11. The piercing needle device of claim 9, wherein movement of the hook along the first motion profile and movement of the lasso along the second motion profile allow the hook and the lasso to entrap a suture positioned proximately to a tip of the medical device.

12. A method of independently controlling at least two implements via a single user action, comprising the steps of:
    providing a medical device including a handle having a first pair of slots and a second pair of slots, an actuator positioned in the handle for movement between a first position and a second, wherein the actuator includes a first groove and a second groove, a first implement connected to a first barrel that extends between and is positioned in the first pair of slots of the handle and is captured in the first groove of the actuator, and a second implement connected to a second barrel that extends between and is positioned in the second pair of slots of the handle and captured in the second groove of the actuator;
    moving a button coupled to the actuator to move the actuator between the first position and the second position so that the first groove drives the first barrel to move within the first pair of slots and the second groove to move within the second pair of slots, wherein movement of the first barrel drives movement of the first implement and movement of the second barrel drives movement of the second implement.

13. The method of claim 12, wherein movement of the first barrel is controlled by a first shape of the first groove and movement of the second barrel is controlled by a second shape of the second groove that is different than the first shape.

14. The method of claim 13, wherein movement of the first barrel is additionally controlled by a first path of the first pair of slots and movement of the second barrel is additionally control by a second path of the second pair of slots that is different than the first path.

15. The method of claim 14, wherein movement of the actuator between the first position and the second position causes the first groove to drive the first barrel to translate along the first path of the first pair of slots and the second groove to drive the second barrel to translate along the second path of the second pair of slots.

16. The method of claim 15, wherein movement of the actuator between the first position and the second position causes the first implement to move in a first motion profile and the second implement to move in a second motion profile that is different than the first motion profile.

17. The method of claim 16, wherein the medical device is a piercing needle.

18. The method of claim 17, wherein the first implement is a hook and the second implement is a lasso.

19. The method of claim 18, wherein movement of the actuator between the first position and the second position causes the hook and the lasso to capture a suture positioned proximately to a tip of the piercing needle.

20. The method of claim 19, wherein the hook and the lasso capture the suture by the hook moving through a first motion profile and the lasso moving through a second motion profile that is different than the first motion profile when the actuator is moved from the first position to the second position.

* * * * *